United States Patent [19]

Dorin et al.

[11] Patent Number: 4,748,234

[45] Date of Patent: May 31, 1988

[54] PROCESS FOR RECOVERING REFRACTILE BODIES CONTAINING HETEROLOGOUS PROTEINS FROM MICROBIAL HOSTS

[75] Inventors: Glenn Dorin, San Rafael, Calif.; Wolfgang H. Hanisch, Balmoral Heights, Australia; Leo S. Lin, Walnut Creek, Calif.

[73] Assignee: Cetus Corporation, Emeryville, Calif.

[21] Appl. No.: 843,997

[22] Filed: Mar. 25, 1986

Related U.S. Application Data

[63] Continuation-in-part of Ser. No. 749,951, Jun. 26, 1985, abandoned.

[51] Int. Cl.$^4$ .......................... C07K 3/12; C07K 3/28; A61K 45/02
[52] U.S. Cl. .................................... 530/412; 530/351; 530/414; 530/416; 530/417; 530/422; 530/424; 530/825; 435/68; 435/70; 424/85
[58] Field of Search ............... 530/351, 412, 414, 416, 530/417, 422, 424, 825; 435/68, 70; 424/85, 811

[56] References Cited

U.S. PATENT DOCUMENTS

| | | | |
|---|---|---|---|
| 4,426,323 | 1/1984 | Jain ........................................ | 435/68 |
| 4,450,103 | 5/1984 | Konrad et al. ....................... | 530/351 |
| 4,462,940 | 7/1984 | Hanisch et al . | |
| 4,464,295 | 8/1984 | Bhaduri ................................. | 424/92 |
| 4,511,502 | 4/1985 | Builder et al. ....................... | 530/351 |
| 4,511,503 | 4/1985 | Olson et al. .......................... | 530/351 |
| 4,512,922 | 4/1985 | Jones et al. ........................... | 530/351 |
| 4,518,526 | 5/1985 | Olson .................................... | 530/351 |
| 4,530,787 | 7/1985 | Shaked et al. ........................ | 530/351 |
| 4,569,790 | 2/1986 | Koths et al. .......................... | 530/351 |
| 4,620,948 | 11/1986 | Builder et al. ....................... | 530/351 |
| 4,656,255 | 4/1987 | Seely .................................... | 530/417 |
| 4,659,568 | 4/1987 | Heilman et al. ..................... | 530/415 |
| 4,675,387 | 6/1987 | Korant ................................. | 424/85 |

FOREIGN PATENT DOCUMENTS

| | | |
|---|---|---|
| 0068691 | 1/1983 | European Pat. Off. . |
| 0114506 | 8/1984 | European Pat. Off. . |
| 8505637 | 12/1985 | World Int. Prop. O. . |

OTHER PUBLICATIONS

Cheng, "Biochem Biophys Res Comm, vol. 111 (1), 1983, pp. 104–111.
Prouty, W. F. et al. (1975), *J. Biol. Chem.* 250:1112–1122, "Degradation of Abnormal Proteins in *Escherichia coli*".
Klier et al. (1982), "Cloning and Expression of the Crystal Protein Genes from Bacillus *Thuringiensis* Strain Berliner 1715" EMBO Journal 1 (7):791–799.
Schnepf et al. (1981), "Cloning and Expression of the *Bacillus Thuringiensis* Crystal Protein Gene in *Escherichia coli*", Proc. Natl. Acad. Sci. USA 78(5), 2893–2897.
Kleid et al. Ch. 25 in *Developments in Industrial Microbiol.* 25:317–325, Society for Industrial Microbiol., Arlington, Va, 1984.
Becker et al., "Downstream Processing of Proteins" *Biotech. Advs.* (1983), 1:247–261.

Primary Examiner—John Kight
Assistant Examiner—Garnette D. Draper
Attorney, Agent, or Firm—Albert P. Halluin; Leona L. Lauder; Jane R. McLaughlin

[57] ABSTRACT

A refractile material containing a heterologous protein is recovered from a host microorganism cell culture transformed to produce the protein. One recovery process involves disrupting the cell wall and membrane of the host cell, removing greater than 99% by weight of the salts from the disruptate, redisrupting the desalted disruptate, adding a material to the disruptate to create a density or viscosity gradient in the liquid within the disruptate, and separating the refractile material from the cellular debris by high-speed centrifugation. Another version of such a recovery process comprises the further steps of solubilizing the refractile material under reducing conditions, organically extracting the solubilized refractile material, and isolating said refractile material from the extractant.

Preferably the protein is recombinant IL-2 or IFN-$\beta$ and the salt removal step is carried out by diafiltration.

46 Claims, 6 Drawing Sheets

FIG. 4

| | |
|---|---|
| Fermentation | |
| Cell concentration | |
| Cell membrane disruption | distilled water |
| Diafiltration | 5 mM EDTA |
| Redisruption | 2 mM EDTA 1% octanol (v/v) |
| Sucrose suspension | 15-35% sucrose (w/w) |
| Centrifugation | 10,000-20,000 x g |
| Solubilization | 5% SDS, phosphate buffered saline |
| Centrifugation | 25,000-35,000 x g |
| Reduction | 5% SDS, 50 mM DTT, 2 mM EDTA pH 8.5 at 50°C for 20 minutes |
| Sephacryl® S200 column | 50 mM acetate, pH 5.5, 0.1% SDS, 1 mM EDTA |
| Oxidation | Iodosobenzoic acid (IBA) 1:1.6 molar protein:IBA, 0.1% SDS, 10 mM phosphate, pH 7.8, 1 mM EDTA |
| Concentration | pH 5.5 |
| Diafiltration | 0.1% SDS, 1 mM EDTA, 50 mM acetate pH 5.5 |
| Filtration | pH ≤ 3, 0.45 μm filter |
| Preparative RP-HPLC | Vydac® C-4 bonded phase silica gel, 2 propanol/acetic acid |
| Dilution | 1:14 into 50 mM acetate, pH 5.5 1.0% SDS, 1 mM EDTA |
| Concentration | |
| Diafiltration | 50 mM acetate pH 5.5, 0.1% SDS, 1 mM EDTA |
| Sephacryl® S200 column | 50 mM acetate pH 5.5, 0.1% SDS, 1 mM EDTA |
| Diafiltration | 10 mM phosphate pH 7.5 |
| Formulation | 5% mannitol (w/v), 10 mM phosphate, pH 7.5 |
| Filtration | 0.45 μm and 0.22 μm filters |
| Lyophilization | |

FIG. 5A

| | |
|---|---|
| Fermentation | |
| Cell concentration | |
| Cell membrane disruption | homogenization |
| Diafiltration | 5 mM EDTA |
| Redisruption | 2 mM EDTA; 1% octanol (v/v); homogenization |
| Sucrose suspension | 15-23% sucrose (w/w) |
| Centrifugation | 10,000 - 15,000 xg |
| Paste solubilization | 2% SDS, phosphate buffered saline |
| Reduction | 10 mM DTT; 2% SDS; 2 mM EDTA; pH 9; heat to 50°C for 10 min. under nitrogen; cool to about 25°C; adjust pH to 7.4 with glacial acetic acid |
| Organic Extraction | 2-butanol/suspension (v/v) |
| Acid precipitation | pH 6.2; 2 mM DTT; 0.1% SDS |
| Centrifugation | 10,000 - 15,000 xg |
| Acid precipitate solubilization | 5% SDS; 5 mM EDTA; 50 mM phosphate buffer |
| Reduction | 20 mM DTT; pH 8.5; heat to 50° for 10 min. under nitrogen; cool to about 25°C |
| Sephacryl® S200 column | 50 mM acetate; pH 5.5; 1% SDS; 1 mM EDTA |
| Oxidation | Iodosobenzoic acid (IBA) equimolar; protein:IBA; 0.1% SDS; 2 mM sodium pyrophosphate; pH 9; 1 mM EDTA |
| Concentration | pH 5.5 |
| Sephacryl® S200 column | 50 mM acetate; pH 5.5; 0.1% SDS; 1 mM EDTA |

FIG. 5B

| | |
|---|---|
| Concentration | |
| Sephadex® G-75 column | 50 mM acetate; pH 5.5; 0.1% SDS; 1 mM EDTA |
| Sephadex® G-25 column | 1 mM NaOH |
| Stabilization | 1.25-5.00%; normal serum albumin (human); pH 11 --> 12.0 --> 7.5 |
| Formulation | 1.25% dextrose |
| Pre-filtration | 0.45 µM |
| Sterile filtration | 0.22 µM |
| Lyophilization | |
| Final container product | |

PROCESS FOR RECOVERING REFRACTILE BODIES CONTAINING HETEROLOGOUS PROTEINS FROM MICROBIAL HOSTS

This application is a continuation-in-part application of U.S. patent application Ser. No. 749,951, filed June 26, 1985 now abandoned.

BACKGROUND OF THE INVENTION

This invention relates to a biochemical separation or recovery process in which refractile bodies containing microbially produced proteins are separated or recovered from the microorganism hosts which produce them.

Many types of proteins, particularly proteins of potential therapeutic use such as interferon (IFN), interleukin-2 (IL-2), feline leukemia virus antigen (FeLV), etc. have been produced from transformed host cells containing recombinant DNA. The host cells are transformed with expression vectors containing genes encoding the desired heterologous protein and are then cultured under conditions favoring production of the desired protein.

Often the heterologous protein produced by the host cell precipitates inside the cell as opposed to being soluble in the cell. The intracellularly produced protein must be separated from the cellular debris and recovered from the cell before it can be formulated into a purified biologically active material.

Procedures for purifying native IL-2 from T cells are described by Watson, J. et al., *J. Exp. Med.* (1979) 150: 849-861; Gillis, S. et al., *J. Immunology* (1980) 124: 1954-1962; Mochizuki, D. Y., et al., *J. Immunol. Meth.* (1980) 39: 185-201; Welte, K. et al., *J. Exp. Med.* (1982) 156: 454-464; EP No. 92,163 and EP No. 94,317. In general, these procedures involve precipitating proteins from culture supernatants with ammonium sulfate followed by a chromatographic fractionation.

U.S. Pat. Nos. 4,450,103 and 4,462,940 and Derynck, R., et al., *Nature* (1980) 287: 193-197 describe procedues for recovering IFN-β from IFN-β-producing *E. coli.* The patents describe procedures in which IFN-β is extracted from cellular material with 2-butanol or 2-methyl-2-butanol.

Commonly owned U.S. Pat. No. 4,569,790, filed Mar. 28, 1984 and issued Feb. 11, 1986 to K. Koths et al., describes a process for recovering IL-2 from an IL-2-producing microorganism whereby the microorganism cell membrane is disrupted, the disruptate is extracted with an aqueous solution of a chaotropic agent such as urea, the IL-2 is solubilized with, e.g., sodium dodecyl sulfate, and the IL-2 is separated in the presence of a reducing agent.

Commonly owned U.S. Pat. No. 4,530,787 filed Oct. 17, 1984 and issued July 23, 1985 to Z. Shaked et al., describes a process for oxidizing recombinant proteins such as IL-2 selectively and stoichiometrically using o-iodosobenzoic acid to ensure that the protein will be functionally equivalent to its native counterpart.

The above techniques for recovering the protein generally require use of costly reagents which must be removed from the protein prior to formulation thereof. Furthermore, many heterologous proteins are precipitated intracellularly in the form of refractile or inclusion bodies which appear as bright spots visible within the enclosure of the cell under a phase contrast microscope at magnifications down to 1000 fold. See. e.g., Miller et al., *Science* (1982) 215: 687-690 Cheng, *Biochem. Biophys. Res. Comm.,* (1983) 111: 104-111. Using the techniques described above, such proteins may not be sufficiently isolated from protein contaminants or from forms of the protein which are biologically inactive when produced intracellularly.

Becker et al., *Biotech. Advs.* (1983) 1: 247-261 disclose separation of these bodies from most of the cell debris and soluble impurities by a low-speed centrifugation. In addition, Kleid et al., ch. 25 in *Developments in Industrial Microbiology,* Vol. 25, p. 317-325 (Society for Industrial Microbiology, Arlington, VA, 1984) disclose purification of refractile bodies by homogenization followed by centrifugation. Also, Marston et al., *Bio/Technology* (September, 1984), pp. 800-804 describe release of inclusion bodies by enzymatic and mechanical disruption procedures as well as sonication. Centrifugation at 12,000 xg for five minutes at 4° C. of the cell lysates removed all the inclusion bodies from the supernatant. The resulting pellets are suspended in Triton X100 and EDTA and centrifuged before denaturation.

Purification and activity assurance of precipitated heterologous proteins is also described by U.S. Pat. Nos. 4,511,502; 4,511,503; 4,512,922; and 4,518,526; and EP No. 114,506. U.S. Pat. No. 4,511,502 describes purifying the refractile protein by isolation thereof from a host cell, dissolving the protein in a strong denaturing solution and removing impurities by high speed centrifugation. U.S. Pat. No. 4,511,503 describes and claims isolating the refractile protein from a host cell and treating the protein with a strongly denaturing solution. U.S. Pat. No. 4,512,922 describes and claims solubilizing the refractile bodies in a strongly denaturing solution and replacing with a weakly denaturing medium. U.S. Pat. No. 4,518,526 describes treating the host cell culture with a buffer of sufficient ionic strength to solubilize the host protein but not the refractile protein, disrupting the cells, and treating the insoluble fraction so as to obtain the refractile protein. EP No. 114,506 discloses a method for treating refractile material containing a heterologous protein so as to recover the protein from its host cell by contacting the refractile material with a denaturing solution which may optionally be contacted with a size-discriminating molecular sieve or subjected to high speed centrifugation to remove high molecular weight components from the solution. The examples of EP No. 114,506 indicate that the process requires repeated runs for successful recovery of product.

There remains a need in the art for a method of recovering refractile material containing heterologous expression products from the host cells which method is less costly, is easier to handle, and results in maximum recovery of pure protein in a biologically active form without use of chemical agents.

SUMMARY OF THE INVENTION

The present invention relates to a recombinant protein recovery process which does not employ costly reagents with their attendant disposal problems, does not require repeated runs, and results in a pure, biologically active protein product.

More specifically, the present invention relates to a process for recovering a refractile material containing a heterologous protein from a host microorganism cell culture transformed to produce said protein, said process comprising:

(a) disrupting the cell wall and cell membrane of the microorganism;

(b) removing greater than 99% by weight of the salts from said disruptate;

(c) redisrupting the desalted disruptate;

(d) adding a material to the disruptate to increase the density or viscosity of, or to create a density or viscosity gradient in, the liquid within the disruptate; and (e) separating the refractile material from the cellular debris by high-speed centrifugation.

In preferred embodiments step (b) is accomplished by diafiltration or centrifugation and step (d) is accomplished by increasing the density or viscosity of the liquid to within certain specified ranges.

The present invention also relates to a process for recovering a refractile material containing a heterologous hydrophobic protein from a host microorganism cell culture transformed to said protein, that encompasses not only steps (a) through (e) as outlined immediately above but also comprises the following steps:

(f) solubilizing the refractile material under reducing conditions;

(g) organically extracting the solubilized refractile material; and (h) isolating said refractile material from the extractant.

In preferred embodiments, step (f) is accomplished with a solubilizing agent in an aqueous buffer in the presence of a reducing agent; step (g) is accomplished by using 2-butanol as the organic extractant; and step (h) is accomplished by employing an acid precipitation step followed by centrifugation.

BRIEF DESCRIPTION OF THE DRAWINGS

FIG. 4 is a flow diagram illustrating the details of each step of one of the preferred entire processes from fermentation of the host culture to lyophilization of the formulated purified protein product.

FIGS. 5A and 5B are flow diagrams illustrating the details of each step of another preferred entire process from fermentation of the host culture to lyophilization of the formulated purified protein product. These figures correspond to the procedure followed in Example V.

DESCRIPTION OF THE PREFERRED EMBODIMENTS

Figure 1:
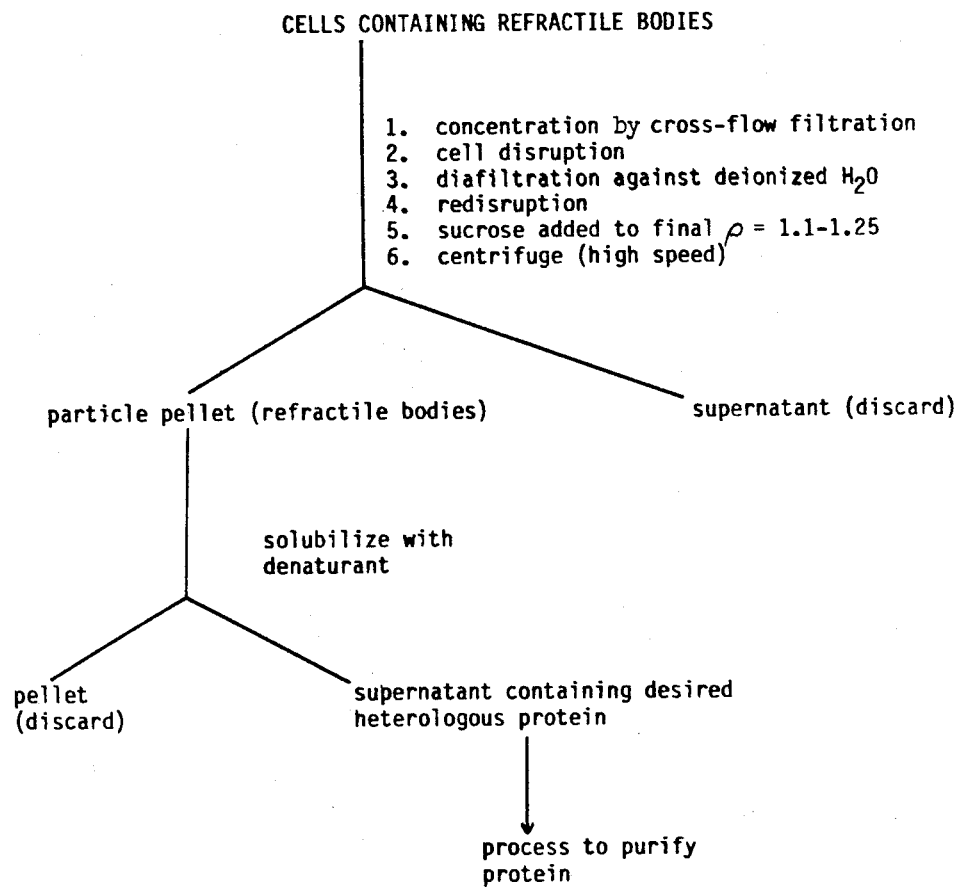
FIG. 1 depicts the general scheme used in Examples I-IV to isolate the heterologous protein.

As used herein, the term "heterologous" proteins refers to proteins which are foreign to the host cell transformed to produce them. Thus, the host cell does not generally produce such proteins on its own. Such proteins are produced by recombinant DNA technology using techniques well known in the art. The proteins herein are often also hydrophobic, i.e., they are not soluble or not readily soluble in aqueous medium under ambient conditions of room temperature and atmospheric pressure at a pH of between about 6.5 and 7.8, i.e., at about neutral or physiological pH.

The heterologous proteins are recovered from refractile materials by the present process. The term "refractile" material designates material or bodies which refract light and appear as bright spots when viewed through a phase contrast microscope. Refractile material is also known as "inclusion" bodies. Examples of heterologous proteins which form refractile bodies in commonly found culture conditions include interleukin-2 (IL-2), interferon-$\beta$ (IFN-$\beta$), envelope protein from feline leukemia virus antigen (FeLV), human growth hormone (hGH), bovine growth hormone (bGH), porcine growth hormone (pGH), and certain proteins coated or fused with a virus such as FMD virus. Certain proteins, such as interferon-$\alpha$ (IFN-$\alpha$), interferon-$\gamma$ (IFN-$\gamma$), and tumor necrosis factor (TNF), are more soluble in the cytoplasm.

The precise chemical structure of the protein will depend on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of protein herein so long as the activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy activity do not remove the protein sequence from the definition.

Finally, modifications to the primary structure itself by deletion, addition, or alteration of the amino acids incorporated into the sequence during translation can be made without destroying the activity of the protein. For example, at least one cysteine residue which is not essential to biological activity, is present in the biologically active protein, and is free to form a disulfide link may be deleted or replaced with another amino acid to eliminate sites for intermolecular crosslinking or incorrect intramolecular disulfide bond formation. Such modified proteins, known as "muteins," are described in U.S. Pat. No. 4,518,584 issued May 21, 1985. In another example, a conservative amino acid of a biologically active protein such as IL-2 or IFN-$\beta$ is substituted for each methionine residue susceptible to chloramine T or peroxide oxidation, wherein additional, non-susceptible methionine residues are not so substituted. A conservative amino acid alteration in this context is defined as one which does not adversely affect biological activity and involves neutral or non-polar amino acid substitutions or deletion of the methionine. In a preferred example of this embodiment the methionine at amino acid position 104 of IL-2 is replaced by an alanine residue.

Preferably the protein herein is IL-2 or IFN-$\beta$. Most preferably the protein is unglycosylated IL-2 which is produced by a microorganism that has been transformed with a human IL-2 gene or a modification of the human IL-2 gene that encodes a protein having: (a) an amino acid sequence that is at least substantially identical to the amino acid sequence of native human IL-2 and (b) biological activity that is common to native human IL-2. Substantial identity of amino acid sequences means the sequences are identical or differ by one or more amino acid alterations (deletions, additions, substitutions) that do not cause an adverse functional dissimilarity between the synthetic protein and the native human IL-2. Examples of such proteins are the IL-2s described in European patent application No. 83101035.0 filed Feb. 3, 1983 (published Oct. 19, 1983 under publication no. 91539) and European patent application No. 82307036.2 filed Dec. 22, 1982 (published Sept. 14, 1983 under no. 88195), the mutein IL-2s described above, and the IL-2s described in the examples of this application.

As used herein the term "transformed" in describing host microorganism cell cultures denotes a microorganism that has been genetically engineered to produce a heterologous protein that possesses the activity of the native protein. Examples of transformed microorganisms are described in the examples of this application. Bacteria are preferred microorganisms for producing the protein. Synthetic protein may also be made by suitably transformed yeast and mammalian cells. *E. coli* is particularly preferred.

FRONT-END PROCESSES

The transformed microorganisms are grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*, Lange Medical Publications, 14th Ed pp. 80-85 (1980).) In expression vectors involving the trp promoter, the tryptophan concentration in the medium is carefully controlled to become limiting at the time protein expression is desired. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by cross-flow filtration, centrifugation, or other conventional methods. Preferably a compound which is non-toxic to humans, such as 1-octanol, in an amount of about 1% by weight of total components, is added to the fermenter before or during cell concentration to ensure that no viable recombinant organisms remain before cell membrane containment is broken.

Following concentration of the harvested culture, the cell membranes of the microorganisms are disrupted. Conventional cell disruption techniques such as homogenization, sonication, or pressure cycling may be used in this step of the process. Preferred methods are sonication or homogenization with a homogenizer. The end point of the disruption step can be determined by monitoring the optical density with the absorbance at 260 nM of the suspension typically increasing with cell lysis. In any event, the disruption should break substantially all of the cells so that substantially no intact cells are carried through to the solubilization step. Before the disruption, the pH of the liquid phase of the concentrate is adjusted, if necessary, to a level that facilitates removal of *E. coli* proteins in subsequent steps, while retaining the heterologous protein as an insoluble complex in the cellular debris.

The steps in the recovery process subsequent to the disruption step are primarily designed to separate the refractile material from the other contaminating proteins and other cellular debris. Using the process herein the refractile bodies can be isolated from the cellular debris to obtain a protein purity of about 50% by weight. Subsequent isolation an purification of the protein using the preferred techniques herein will yield a product of at least 95% purity, preferably at least 98% purity, in good yields. Simultaneously, this purification process also reduces pyrogenic substances in the final product to a level believed to be acceptable for parenteral administration to patients.

After the cells have been disrupted, deionized water is preferably added to the disruptate and greater than 99% by weight of the salts are removed therefrom. The salts are water-soluble materials composed of oppositely charged small molecular weight ions. The removal of these salts to reduce the ionic strength of the disruptate may be accomplished by diafiltration using deionized water to flush out the ions or by centrifuging to pellet the cellular debris and refractile bodies followed by resuspension in deionized water. If diafiltration is employed, preferably deionized water is continuously added such that the rate of addition of water equals the filtration rate.

After the salts are essentially removed, optionally a compound such as 1-octanol may be added to the desalted disruptate, if not added earlier, to ensure that no viable recombinant organisms remain before containment is broken. The desalted disruptate is again disrupted as described above for the initial disruption.

After redisruption, density or viscosity is increased and/or a gradient is created during centrifugation in the liquid within the disruptate by adding a material to the disruptate. There are several means to accomplish this purpose, all relying on the sedimentation characteristics of the particles by varying the density and/or viscosity of the liquid phase. One means to accomplish this goal is to add a material which increases the density of the liquid to a $\rho$ of about 1.1 to 1.3 g/ml, preferably 1.13 to 1.17 g/ml.

Materials which may be used to acomplish this density increase include a sugar or mixture of sugars, such as, e.g., sucrose, dextrose, fructose, maltose, maltotriose, and other mono-, di- or polysaccharides. Most preferably the sugar is sucrose. Alternatively, a two-phase system of materials such as, e.g., a glycerol/sucrose mixture may be used wherein the disrupted particles partition to the interface between the heavy and light phases and can be eluted by a liquid/liquid separation.

In addition, the viscosity of the liquid phase may be increased to from 5 to 10 cps by any suitable means such as by adding a viscous compound such as, e.g., sucrose or glycerol thereto. Also, a gradient is created if, e.g., the particles are in a 60% aqueous glycerol suspension while the centrifuge bowl contains 80% aqueous glycerol.

In the final step of the abbreviated "front-end" process to recover the refractile bodies, the refractile bodies containing the desired protein are separated from the cellular debris by high-speed centrifugation. By "high-speed centrifugation" is meant spinning the suspension in a centrifuge at about 10,000 to 40,000 times gravity, preferably about 10,000-20,000×g, for a suitable time period depending on the volume, generally about 10 minutes to seventy-two hours. The density of the medium will generally be too high to separate the particles by low-speed centrifugation. Therefore, if the centrifugation is carried out at low speeds (e.g., at 500 to 5,000×g), satisfactory results are not obtained. The exact centrifuge speed will depend on the protein and the final concentration of material added to create the gradient (e.g., sucrose). For example, interferon may require lower sucrose concentrations to obtain maximal recovery, and thus the centrifugation speed may be lowered, or the centrifuge retention time decreased.

FIG. 1 illustrates one preferred scheme for obtaining the desired protein contained within the refractile bodies. In this scheme the cells containing refractile bodies are concentrated by cross-flow filtration and disrupted. Then the disruptate is diafiltered against deionized water to reduce the ionic strength of the liquid and then redisrupted. Sucrose is then added to obtain a final density of the liquid of $\rho = 1.1$ to 1.3. The mixture is then centrifuged using high-speed centrifugation to obtain a pellet containing the refractile bodies and a supernatant which is discarded. This pellet can be differentiated as the "particle pellet" or "particle paste" from that of the "final" pellet or "final paste" resulting from the alternative, expanded "front-end" process, described below.

Figure 2:
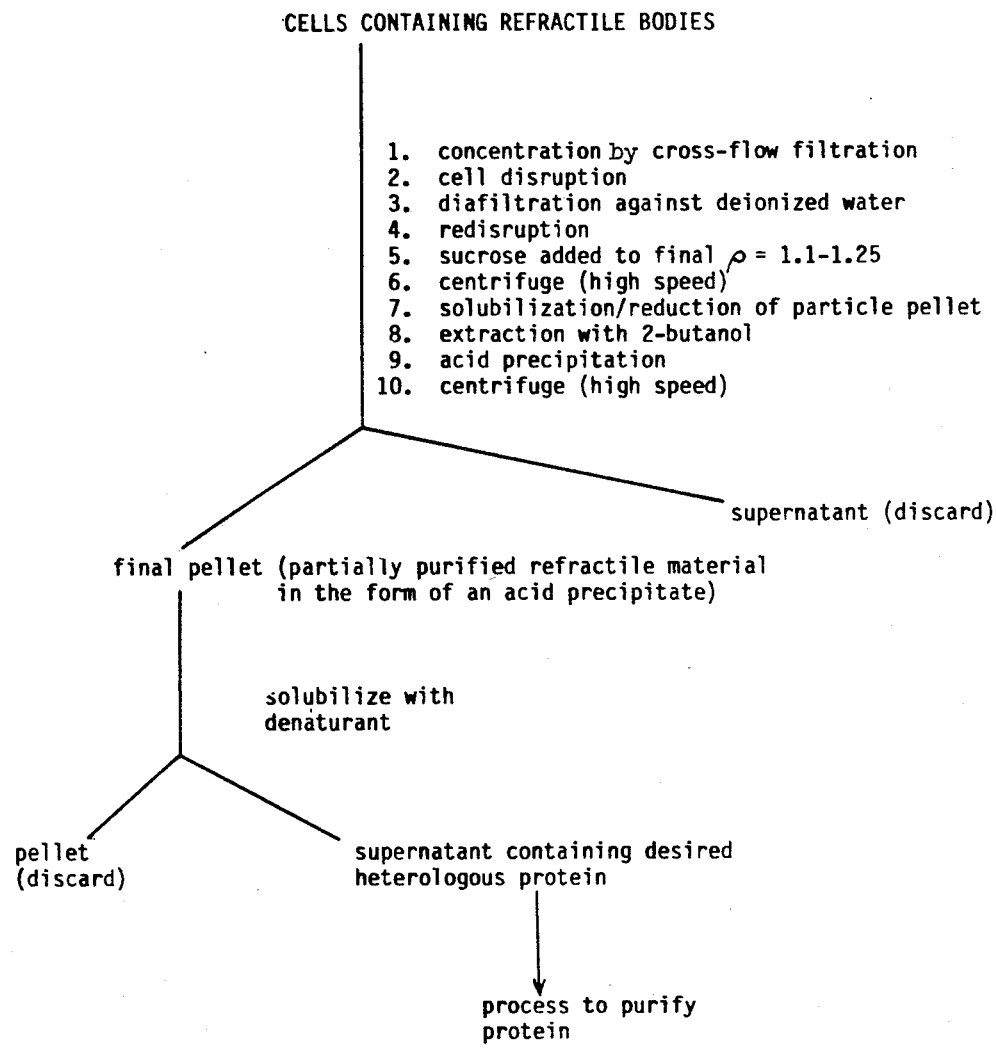
FIG. 2 depicts an alternative general scheme, as used in Example V, to isolate a heterologous protein.

An alternative, expanded "front-end" process to recover the refractile bodies is schematically illustrated in FIG. 2. In this scheme, the particle pellet obtained from the centrifugation step (6) in FIG. 1 is solubilized, reduced and then extracted from the aqueous medium with 2-butanol. The extractant phase is then precipitated with an acid and centrifuged to produce a "final pellet" or "final paste" which is then further purified as indicated. Example V exemplifies the expanded front-end process.

The particle pellet resulting from the centrifugation at the end of the abbreviated front-end process contains approximately 15-70% by weight of the desired heterologous protein as determined by Lowry assay [Lowry et al., *J. Biol. Chem.* (1951) 193: 265-275]. The final pellet from the expanded front-end process contains about 70-85% by weight of the desired protein.

The alternative, expanded front-end process is distinguished from the abbreviated front-end process in that it comprises several additional steps as follows: solubilizating the refractile bodies under reducing conditions; organically extracting the solubilized refractile material; and isolating said refractile material from the extractant. These alternative front-end steps can be done to promote recovery of any of the above-mentioned candidate heterologous proteins that are deposited within the host strain in refractile bodies. Essentially, the enhanced purity of the final pellet as opposed to the particle pellet lessens the purifying burden of downstream processing. There is an interdependence between the choice of the front-end process and later process purification steps to achieve the desired purity level for the final product. Once the choice of the particular front-end recovery of the refractile bodies has been made, one skilled in the art can pick and choose the alternative purifying steps outlined below to achieve the desired purity level of the final product.

The organic extraction of the expanded front-end primarily effects a partition of the hydrophobic proteins from the lipopolysaccharides and nucleic acids of the aqueous and solid phases. Secondarily, said extraction also removes some of the host cell's endotoxins and other proteins. The isolation step, preferably by acid precipitation followed by centrifugation, separates the refractile material from the organic extractant and other cellular debris.

For solubilizing the particle pellet of the expanded front-end, the following solubilizing agents can be used: sodium dodecyl sulfate (SDS), sodium laurate, urea, sodium dodecyl sulfonate, sodium decyl sulfate, sodium tetradecyl sulfate, sodium tridecyl sulfonate, sodium myristate, sodium caprate, sodium dodecyl N-sarcosinate, and sodium tetradecyl N-sarcosinate. Preferred solubilizing agents are SDS or sodium laurate. Most preferred is SDS.

The solubilizing agent is in an aqueous buffer, preferably phosphate buffered saline. The preferred percentage of the solubilizing agent is in the range of 1% to 5% (w/v). (Percentages herein reflect weight to volume ratios.) The most preferred solubilizing solution is phosphate buffered saline with 2% SDS.

Reducing agents that can be employed during the solubilization step include: mercaptoethanol, glutathione, cysteine and dithiothreitol (DTT). DTT is the most preferred reducing agent. The concentration of the reducing agent in the medium will usually range between about 5 to 20 mM with approximately 10 mM being the most preferred concentration.

Reduction conditions may also include the addition of a chelating agent such as ethylenediaminetetraacetic acid (EDTA) in concentrations ranging between 1 and 5 mM with approximately 2 mM being the most preferred concentration. It is also preferable to carry out the reduction at an alkaline pH usually ranging between 8.5 and 9.5 with a pH of 9 being especially preferred. The pH adjustment may be accomplished by the addition of a base such as NaOH.

Further, it is preferable to carry out the reduction reaction at an elevated temperature, preferably at 45°-55° C. and most preferably 50° C., under nitrogen to ensure efficient reduction of the material. The reaction will typically be run from between 5 and 15 minutes, most preferably for 10 minutes.

After the reduction is complete, it is usually cooled to approximately 25° C. and the pH adjusted with an acid, preferably glacial acetic acid, to a pH of between 7 and 7.8, most preferably 7.4. Once said solubilization and reduction steps are complete, the organic extraction is begun.

The organic extractant can be 2-butanol, 2-methylbutanol or mixtures thereof. Most preferably the extractant is 2-butanol. The conditions for extraction would be those that maintain phase separation between the aqueous medium and the extractant.

The extractant will normally be combined with the aqueous solution of the protein in volume ratios in the range of about 0.8:1 to about 3:1, preferably about 1:1 (extractant: volume of the suspension). The extraction may be carried out using conventional batch or continuous liquid-liquid extraction techniques and equipment. The extraction may be carried out at 20° C. to 100° C. and involve contact times in the range of about one minute to one hour.

Upon completion of the extraction, the aqueous phase and extractant phase are separated, and then the desired protein is isolated from the extractant phase. Various isolation techniques such as precipitation, molecular sieve chromatography, affinity chromatography, and electrophoresis can be employed.

A preferred isolation technique is an acid precipitation step followed by centrifugation. The extracted refractile material containing the desired heterologous protein is precipitated from the extractant by mixing the extractant solution with an aqueous buffer containing a solubilizing agent in a phosphate buffered saline under reducing conditions. The preferred solubilizing agent is SDS at a concentration of from about 0.05 to 0.2%, most preferably at 0.1%.

The reducing agent added to the organic extract-/buffer solution may be mercaptoethanol, glutathione, cysteine or dithiothreitol (DTT), DTT being the most referred. The final concentration of the reducing agent can be in the range of 1 mM to 5 mM with 2 mM of DTT being the most preferred.

The pH of the organic extract/buffer solutions is then reduced with an acid typically to the range of about 5 to 6.5. This pH adjustment is most preferably carried out with glacial acetic acid to a pH of about 6.2.

The precipitated mixture is then centrifuged at a high speed, preferably at 10,000 to 15,000×g, preferably for a time period ranging from 15 minutes to 10 hours, depending upon the size of the fermentation run. For a 1000-liter run, as exemplified in Example V, the preferred centrifuging time would be 10 hours.

Such centrifuging is the last step of the expanded front-end process resulting in the final pellet or final paste. Whether the abbreviated front-end or expanded front-end are the choice for recovering refractile bodies containing the desired heterologous protein, the next step in purification would be solubilization of the refractile bodies as noted below.

DOWNSTREAM PROCESSING

After the last centrifugation step of either the abbreviated front-end process or the expanded front-end process, a pellet, particle or final, is the result containing refractile material at different loads of purity, 15–70% or 70–85% purity, respectively, of the desired heterologous protein. Whether the abbreviated or expanded version of the front-end process, the next step in the purification process is the solubilization with a denaturant of either the particle pellet or the final pellet.

The pellets containing the refractile bodies obtained after centrifugation are preferably solubilized by contact with a neutral aqueous buffer containing not only the protein denaturant (solubilizing agent) but also a reducing agent. Surface active agents (detergents) which have a suitable hydrophobic-hydrophilic balance to solubilize the hydrophobic protein may be used as solubilizing agents. Strong protein denaturants such as alkali metal sulfates containing 10 to 14 carbon atoms and alkali metal alkyl sarcosinates are preferred solubilizing agents, with SDS and sarcosyl being particularly preferred. Optionally, said aqueous buffer can also contain a chelating agent in a concentration of from 3 to 7 mM. Most preferably, said chelating agent would be EDTA at a concentration of 5 mM.

The amount of solubilizing agent used in the solubilization will depend upon the particular agent. When SDS or sarcosyl is used, the preferred concentration (w/v) of SDS/sarcosyl is 1–10% in buffer such as phosphate buffered saline (50 mM sodium phosphate, pH 7, 0.9% sodium chloride). Preferaby the range of SDS would be from 2 to 7%, most preferably 5%. The solubilizing medium may also contain a sufficient amount of reducing agent to prevent the solubilized protein from undergoing oxidation to any significant degree. Protein reducing agents such as dithiothreitol (DTT) and 2-mercaptoethanol may be used for this purpose. The concentration of reducing agent such as DTT in the medium will usually range between about 5 to 30 mM, most preferably 20 mM. The solubilization will typically be carried out at temperatures in the range of 20° C. to 25° C. with mixing to facilitate contact between the solid phase and the solubilizing medium. Optionally, a reduction step may be carried out at this point. The pH, if necessary, may be adjusted to a range of 8 to 9, most preferably approximately 8.5. The suspension may be heated to 50±5° C. for 5 to 15 minutes under nitrogen. The reaction mixture would then be cooled to approximately 25° C.

The solubilization is considered complete when the sample has sat 15 minutes or the solution turns translucent. Optionally at this point, the insoluble material may be separated by centrifugation or filtration after completing the solubilization.

After the protein is solubilized, the resulting suspension may optionally be centrifuged at 10,000–40,000×g, preferably 25,000 to 35,000×g, to obtain a pellet containing, inter alia, additional host (e.g., $E.$ $coli$) proteins, notably including certain contaminants that have molecular weights very close to that of the desired protein. The exact speed of centrifugation is not critical, as most of the insoluble material will come out, even at low speeds. The pellet is discarded and the supernatant containing the desired protein is retained and processed to recover the desired protein. Otherwise, after the solubilization or solubilization/reduction step, the pH of the suspension can be adjusted to a pH of approximately 5 to 6, most preferably 5.5 with glacial acetic acid, and then filtered.

If a reduction step was not carried out during the solubilization, the next step in the process would be a reduction of the solubilized refractile body protein. A preferred reducing agent is diothiothreitol (DTT) which for this purpose may be added to a final concentration ranging from 10 to 100 mM, most preferably from 20 to 50 mM. Reduction conditions may also include the addition of a chelating agent such as ethylenediaminetetraacetic acid (EDTA) in concentrations ranging between 1 and 5 mM. It is also preferable to carry out the reduction at a somewhat alkaline pH usually ranging between 8 and 9.5, with a pH of 8.5±0.1 being especially preferred. This pH adjustment may be accomplished by the addition of a base such as NaOH. Furthermore, it is also preferable to carry out the reduction reaction at an elevated temperature under nitrogen to ensure efficient reduction of the material. The reaction will typically be run at 45° to 55° C. for 5 to 30 minutes under nitrogen. Especially preferred is a reaction time of from 10 to 20 minutes. After the reduction is complete it is usually cooled to about 25° C. and the pH is adjusted to a range of 5 to 6 using an acid such as glacial acetic acid. Most preferably the pH would be adjusted to 5.5.

The next step in the process is to separate the protein in the supernatant from any host contaminants remaining after the centrifugation or filtration and optimally from the solubilizing agent. Gel filtration chromatography, reverse-phase high performance liquid chromatography (RP-HPLC), or a combination of gel filtration chromatography and RP-HPLC, can be used. The gel filtration chromatography is preferably carried out in two stages that remove both pyrogenic components and protein contaminants having molecular weights higher or lower than that of the protein. Gels that are capable of fractionating the solution to permit separation of the protein from these contaminants are commercially available. Sephacryl ®S-200 is a preferred gel for removing the higher molecular weight components and Sephadex ®G-25, G-75 or G100 gels are preferred for removing the low molecular weight contaminants. The gel filtrations will typically be run in buffered solutions (pH 5.5 to 7.0) containing about 0.1% to 1.5% solubilizing agent and about 0.5 to 10 mM reducing agent. The column will be sized to permit suitable resolution of the desired components.

RP-HPLC is an alternative to gel filtration. Also, RP-HPLC is capable of removing molecules from the solution that have molecular weights close to the protein and cannot, therefore, be removed completely by gel filtration. In addition, contaminants such as bacterial endotoxin are also removed effectively by RP-HPLC. Therefore, RP-HPLC may also be used as a final purification step after gel filtration. U.S. Pat. No. 4,569,790 to K. Koths et al. discloses the following preferred materials and methods for the purification of Il-2 by RP-HPLC. Supports (stationary phases) that provide good resolution of proteins may be used in the RP-HPLC. C-4, C-8, or C-18 on 300 angstrom pore-size supports are examples of preferred supports. The separation is carried out at a pH of approximately 5.5, in order to keep the protein in solution. In this regard, the pH of the protein solution will preferably be adjusted to this range. The solution is loaded into the RP-HPLC column and is adsorbed onto the stationary phase. A gradient solvent system comprising an organic acid such as acetic acid or trifluoroacetic acid and organic solvent such as propanol or acetonitrile is used to elute the protein from the column. Acetic acid-propanol, trifluoroacetic, acid-propanol, and trifluoroacetic acid-acetonitrile are preferred solvent systems. IL-2 elutes in the acetic acid-propanol system at about 40% propanol, in the trifluoroacetic acid-propanol system at about 50% propanol, and in the trifluoroacetic acid-acetonitrile system at about 62% acetonitrile. For convenience, the organic solvent content of the eluant will usually be increased rapidly to a level somewhat below the solvent concentration at which the protein elutes followed by a slow gradient change in the range of about 0.1% to 1.0%/min.

As soon as the protein is recovered from the chromatography step, it is lyophilized and resuspended in a neutral aqueous buffer containing the reducing agent (to keep the protein in a reduced state) and the solubilizing agent (to keep it in solution). The IL-2 is stable in this form and may be stored for further treatment and formulation before being used.

An alternative and preferred procedure is to oxidize selectively, under controlled conditions, the protein after it has been separated by gel filtration, as described in U.S. Pat. No. 4,572,798 filed Dec. 6, 1984 and issued Feb. 25, 1986 to K. Koths et al. (using an oxidation promoter containing a $Cu^{+2}$ cation) and in U.S. Pat. No. 4,530,787 filed Oct. 17, 1984 and issued July 23, 1985 to Z. Shaked et al. (using o-iodosobenzoic acid), the disclosures of which are incorporated herein by reference and described hereinabelow, and purify the oxidized product by RP-HPLC or gel filtration followed by RP-HPLC. Preferred oxidizing agents for this purpose are $CuCl_2$ and o-iodosobenzoic acid. The $Cu^{+2}$ oxidation comprises reacting an aqueous solution containing a solubilized form of the recombinant protein at a pH between about 5.5 and 9 in the presence of air with at least an effective amount of an oxidation promoter containing a $Cu^{+2}$ cation. Controlled oxidation causes the formation of disulfide bridging in the recombinant protein which conforms to the bridging in its native counterpart with no or minimal overoxidation and formation of nonconforming bridging or oligomers. Such oxidation enables the production of high yields of the recombinant protein in a configuration that most closely resembles the configuration of its native counterpart, thereby ensuring the likelihood that the recombinant protein will be functionally equivalent to the native protein.

The amount of oxidant or oxidation promoter employed is at least an effective amount for oxidation, i.e., an amount which at minimum will be necessary to conduct the oxidation reaction effectively within a convenient period of time. An effective amount is the amount approximately equivalent to the concentration of free sulfhydryl groups on the protein which are destined to be involved in forming the desired disulfide bonds. Preferably, the amount of $CuCl_2$ will range from about 1 to 400 micromolar, depending on the protein concentration, more preferably 5 to 50 micromolar if the protein is IL-2. In the case of o-iodosobenzoic acid the mole ratio of oxidant to protein will preferably be in the range of about 0.05:1 to about 5:1, most preferably about 0.8:1 to about 1:2. The concentration of protein in the reaction mixture is kept low, i.e., generally less than about 5 mg/ml, preferably about 0.05 to about 2 mg/ml, and more preferably about 0.1 to about 1 mg/ml, to reduce the likelihood of oligomer formation.

The pH of the reaction medium for $Cu^{+2}$ oxidation is generally maintained at a level between about 5.5 and 9, preferably 6 and 8, and more preferably about 7.

The pH of the reaction medium for o-iodosobenzoic acid is maintained at a level at least about one-half pH unit below the $pK_a$ of the cysteine residues being oxidized. When the $pK_a$s of these residues differ, the pH is preferably maintained at least about one-half pH unit less than the $pK_a$ of the cysteine residue having the lowest $pK_a$. Control of the pH in this manner for o-iodosobenzoic acid oxidation controls the amount of nonionized thiol, thereby controlling the rate of the reaction and favouring the formation of the desired disulfide bridging. For recombinant IFN-$\beta$ the pH for o-iodosobenzoic acid oxidation is maintained between 6 and 9, preferably 7.0 and 9.0. For recombinant IL-2, it is maintained between 5.5 and 9, preferably 7.0 and 8.0.

The reduced, cloned protein, which is less soluble than the oxidized form of the protein, generally must remain in solution, i.e., be in solubilized form, for effective oxidation to occur. Therefore, the reaction mixture with $Cu^{+2}$ will preferably also contain at least an effective amount of a solubilizing agent to prevent the protein from precipitating out of solution. As used herein, the term "solubilizing agent" refers to an ionic or nonionic protein-solubilizing solute such as, e.g., sodium dodecyl sulfate (SDS) or urea. The amount of solubilizing agent which may be employed for this purpose is generally from about 0.05 to about 1% by weight per volume (for detergents), most preferably 0.1% of about 5–9M (for urea), depending mainly on the protein and types of oxidation promoter used.

The oxidation reaction time will depend, for example, upon the concentration of reagents in the reaction mixture, the reaction temperature, and the types of reagents. The reaction temperature will normally be between about 20° C. and 40° C., conveniently room temperature, to maintain the solubilizing agent/protein mixture in solution. For $Cu^{+2}$ oxidation, increasing the reaction temperature increases the rate of reaction. The oxidation reaction may be effectively terminated by, e.g., lowering the pH to a level at which the reaction ceases, freezing the solution, or adding chelators such as EDTA to the reaction mixture. Following the reaction, residual oxidation promoter and undesired isomers or oligomers may be removed by selective ultrafiltration or chromatographic techniques. If necessary, the oxidized protein may be purified further from side products and any residual reduced protein using protein purification procedures such as reverse phase high performance liquid chromatography (RP-HPLC).

The purity of the protein after the chromatography step(s) is at least about 95% and usually at least about 98%. This highly pure material contains less than about 5 ng endotoxin, usually less than about 0.01 ng endotoxin per 100,000 units protein bioactivity.

The formulation of the protein in accordance with this invention may be carried out as a separate operation using purified, selectively oxidized protein or in an operation that is integrated with the purification of the selectively oxidized protein. In the latter case, the starting material for the formulation is a protein-containing product from a RP-HPLC treatment of the selectively oxidized product. Preferably a product selectively oxidized by the RP-HPLC product (pool) will comprise a solution of the protein in a water-organic solvent mixture. The nature of the organic solvent will depend upon the solvent system used in RP-HPLC. Examples of systems that may be used for the preparation of IL-2 as described in U.S. Pat. No. 4,569,790 to K. Koths et al. are combinations of an organic acid such as acetic acid or trifluoracetic acid and organic solvent such as propanol or acetonitrile.

Optionally, the first step in one formulation of the protein from such an RP-HPLC pool is to render the mixture aqueous by resuspending (diluting) the pool in an aqueous buffer containing a detergent, such as SDS or sarcosyl, which enhances the solubility of the protein in water. Following this dilution the organic phase is removed from the protein-containing aqueous phase and the detergent concentration is reduced by diafiltration using an appropriate buffer. When SDS is used, the SDS is reduced to a level of about 100 to 250, preferably approximately 200, $\mu g/mg$ when IL-2 is used as protein. Following diafiltration, the protein concentration is readjusted to a concentration in the range of about 0.01 to 10 mg/ml depending mainly on the protein and its intended use, preferably 0.01 to 2 mg/ml for IL-2, and the water-soluble carrier is added to the desired level. The carrier will typically be added such that it is present in the solution at about 1 to 10% by weight, preferably about 5% by weight. The exact amount of carrier added is not critical. Conventional solid bulking agents that are used in pharmaceutical tablet formulations may be used as the carrier. These materials are water soluble, do not react with the protein, and are themselves stable. They are also preferably non-sensitive to water (i.e., nonhygroscopic). Specific examples of carriers that may be added include dextrose, lactose, mannitol, and other reduced sugars such as sorbitol, starches and starch hydrolysates derived from wheat, corn, rice, and potato, microcrystalline celluloses, and albumin such as human serum albumin. Mannitol and dextrose are preferred.

The carrier adds bulk to the formulation such that when unit dosage amounts of the solution are lyophilized in containers, such as sterile vials, the freeze-dried residue will be clearly discernible to the naked eye. In this regard the preferred carrier, mannitol, yields an aesthetically acceptable (white, crystalline) residue that is not sensitive to water. The nonsensitivity of mannitol to water may enhance the stability of the formulation.

Alternatively, the first step in another preferred formulation of the desired protein is a stabilization step. Alpha-interferons and native beta-interferons are not lipophilic proteins. Therefore, they can be stabilized and solubilized by adding a stabilizer such as human serum albumin at a physiological pH. In contrast, lipophilic proteins such as recombinant beta-interferon and interleukin-2 are not solubilized by addition of human serum albumin at pH 6.8-7.8.

Copending, commonly owned, U.S. patent application Ser. No. 775,751, filed Sept. 13, 1985, entitled *An Improved Formulation for Lipophilic Proteins* (Hanisch et al.) outlines an improved process for recovering and purifying lipophilic recombinant proteins such as human $\beta$-interferon and interleukin-2 from their hosts to yield a protein preparation which may be formulated into a stable pharmaceutical composition. Such a composition carrying a therapeutically effective amount of the biologically active recombinant lipophilic protein dissolved in a non-toxic, inert, therapeutically compatible aqueous-based carrier medium at a pH of 6.8 to 7.8 also contains a stabilizer for the protein, such as human serum albumin, normal serum albumin and human plasma protein fraction. The formulation aspects of said U.S. Ser. No. 775,751 are herein incorporated by reference as alternative formulation routes for lipophilic proteins which were recovered as refractile bodies by the abbreviated or expanded versions of the front-end processes of the present invention. The 775,751 application outlines a low pH formulation process.

U.S. Pat. No. 4,462,940, filed May 18, 1983, and issued July 31, 1984 to Hanisch et al., outlines a high pH formulation process, and the formulation aspects thereof are herein also incorporated by reference.

After adding the carrier the unit dosage amounts (i.e., for IL-2 volumes that will provide 0.01 to 2 mg, preferably 0.2 to 0.3 mg, IL-2 per dose) of the solution are dispensed into containers, the containers are capped with a slotted stopper, and the contents are lyophilized using conventional freeze-drying conditions and apparatus.

The lyophilized, sterile product consists of a mixture of (1) protein, (2) carrier (dextrose or mannitol), (3) detergent (SDS), and (4) a small amount of buffer that will provide a physiological pH when the mixture is reconstituted. The product may also contain a minor amount of a preservative to enhance chemical stability. If the protein is IL-2, the recombinant IL-2 will typically constitute about 0.015% to 3.85% by weight of the mixture, more preferably about 0.4% to 0.6% of the mixture. Storage tests of this product indicate that the IL-2 is stable in this form for more than three months at 2° C. to 8° C.

The lyophilized mixture may be reconstituted by injecting a conventional parenteral aqueous injection such as distilled water for injection, Ringer's solution injection, Hank's solution injection, dextrose injection, dextrose and salt injection, physiological saline injection, or the like, into the vial. The injection should be added against the side of the vial to avoid excess foaming. The amount of injection added to the vial will typically be in the range of 1 to 5 ml, preferably 1 to 2 ml.

In an alternative formulation, described in copending U.S. Application Ser. No. 749,955, filed June 26, 1985, that is, filed concurrently with the parent application of the instant application (U.S. Ser. No. 749,951), now abandoned in favor of U.S. Ser. No. 866,459, filed May 21, 1986, and entitled "Solubilization of Proteins For Pharmaceutical Compositions Using Homopolymer Conjugation" to M. Knauf et al., the common disclosure of which is incorporated herein by reference, the hydrophobic protein may be solubilized, not by a detergent, but by reacting the protein with an activated homopolymer selected from polyethylene glycol, polypropylene glycol or polybutylene glycol, said homopolymer having a molecular weight of from 500 to 20,000 daltons, preferably 2000 to 10,000 daltons. The homopolymer is activated by conjugation with a coupling agent having terminal groups reactive with both the free amine or thiol groups of the protein and the hydroxyl group of the homopolymer. Examples of such coupling agents include hydroxynitrobenzene sulfonic ester, cyanuric acid chloride, and N-hydroxysuccinimide. This modification eliminates the necessity for adding detergents to solubilize the protein at physiological pH. The protein is then formulated directly with the water-soluble carrier and buffer as described above, the formulation is lyophilized, and the lyophilized mixture may be reconstituted as described above.

FIG. 4 illustrates a flow diagram of one preferred scheme for obtaining the desired protein, from fermentation to lyophilization. FIGS. 5A and 5B illustrate another preferred scheme.

The reconstituted formulation prepared as described above is suitable for parenteral administration to humans or other mammals in therapeutically effective amounts (i.e., amounts which eliminate or reduce the patient's pathological condition) to provide therapy thereto, the type of therapy being dependent on the type of protein. For example, IL-2 therapy is appropriate for a variety of immunomodulatory indications such as T cell mutagenesis, induction of cytotoxic T cells, augmentation of natural killer cell activity, induction of IFN-gamma, restoration or enhancement of cellular immunity (e.g., treatment of immune deficient conditions), and augmentation of cell-mediated anti-tumor activity. IFN-$\beta$ therapy is appropriate for anti-cancer, anti-viral and anti-psoriasis treatment.

The following examples further illustrate the invention process. These examples are not intended to limit the invention in any manner. In these examples all temperatures are in degrees Celsius unless otherwise indicated.

EXAMPLE I

Procedure for the Purification of Refractile Bodies

A. Cell Growth

E. coli K-12/MM294-1, which were deposited with the American Type Culture Collection in Rockville, MD under ATCC No. 39,515, and were transformed with recombinant plasmid pBR322 carrying heterologous genes under E. coli trp promoter-operator control, exemplified below, were grown in a 10- or 1000-liter fermentor at 37° C. The dissolved oxygen was maintained at about 40% by, as necessary, (1) increasing agitation; (2) adding air; and (3) adding oxygen. The growth medium was the following:

| Ingredient | Concentration |
| --- | --- |
| $(NH_4)_2SO_4$ | 72 mM |
| $KH_2PO_4$ | 21 mM |
| $MgSO_4.7H_2O$ | 3 mM |
| $Na_3$ citrate .$2H_2O$ | 1.5 mM |
| $MnSO_4.4H_2O$ | 30 $\mu$M |
| $ZnSO_4.7H_2O$ | 30 $\mu$M |
| $CuSO_4.5H_2O$ | 3 $\mu$M |
| L-tryptophan | 70 mg/L |
| $FeSO_4.7H_2O$ | 72 $\mu$M |
| thiamine .HCl | 20 mg/L |
| glucose | 5 g/L |
| tetracycline | 5 mg/L |
| pH controlled at 6.8 with KOH | |

A glucose feed was also employed to maintain glucose concentration between 5-10 g/L. The inoculum was 2 mg/L from either frozen or seed cultures. Induction of heterologous protein production by depletion of L-tryptophan from the culture medium occurred at about $OD_{680}=10$ followed by the addition of casamino acids to a final concentration of 2% at $OD_{680}=15$. Cultures were harvested 3-5 hours later.

B. Isolation of Heterologous Protein

The general purification scheme for a heterologous protein utilizing refractile body isolation is diagrammed in FIG. 1. The selection of the denaturing agent in solubilizing the desired protein from the inclusion body preparation as well as the additional steps required in the purification process will be dependent upon the nature of the protein and have been described to some extent by Marston, et al. supra and Kleid, et al., supra. Details of the invention, however, will be similar in all cases and are described below.

1. 10-L Scale

After a 10-L fermentation, cells were concentrated about 10-fold using a hollow fiber membrane cartridge. In addition, cells were washed with 1 L of deionized water. EDTA was added to 25 mM and cells were disrupted by 3 passes at 7500 psi in the homogenizer with brine cooling. The system was rinsed with 0.5 L deionized water and deionized water was added to a final volume of 3 L (Disruptate 1). This lysate was concentrated to 2 L in a housing with a cassette (0.45 micron) followed by diafiltration versus 5 volumes of 5 mM EDTA (diafiltered disruptate). The retentate was concentrated to approximately 1 L and the system was rinsed with 0.5 L deionized water. The concentrated retentate was redisrupted by 5 passes at 7500 psi in the homogenizer with brine cooling to ensure complete cell lysis (Disruptate 2).

The homogenizer was rinsed with an equal volume plus 0.1 L 63% sucrose and 2 mM EDTA resulting in about 33-35% final sucrose composition. The final solution density should be between 1.1 and 1.25 g/ml. The temperature and weight of a 10 ml sample of a disruptate was recorded. A temperature of at least 20° C. was maintained prior to centrifugation. The mixture was centrifuged at 12,000×g at 75 mls/min±5 mls/min. The supernatant was hazy but not turbid (Supernatant 1).

The supernatant was decanted and the pellet was removed into a beaker and weighed. The pellet was resuspended in 1.5 L 10 mM EDTA with a probe (Resuspension 1) and recentrifuged at the same temperature and flow rate used previously. The supernatant was again decanted (Supernatant 2) and the pellet containing purified refractile body particles (Final Pellet) was stored as frozen paste at −80° C. Refractile particle preparations were characterized by Lowry assay of total protein bioactivity, SDS-PAGE, and lipopolysaccharide assay.

1. 1000-L Scale

The purification scheme for the isolation of refractile bodies from 1000-L of culture is essentailly the same as that described for the 10-L scale except for the use of larger scale equipment. Cultures were concentrated by cross-flow filtration using a spiral cartridge. Cells were disrupted by 3 passes through a disruptor at about 6500 psi. After diafiltration versus deionized water, EDTA was added to a final concentration of 2 mM. To ensure that no viable recombinant organisms remained before containment was broken, 1 L of octanol was also added to the fermenter. After several hours, the diafiltered disruptate was again disrupted by one pass through the disruptor.

Sucrose was added to the disruptate to give a final due to a low BSA standard, thus resulting in a lower apparent IL-2 contribution to the total particle protein. From densitometry scanning of SDS-PAGE resolution of refractile body protein, IL-2 may represent as much as 85% of the total refractile body protein. This is generally a less accurate means of estimating refractile body protein composition since densitometric absorption depends on the amount of Coomassie dye bound to a protein which varies among different proteins (per unit mass). At any rate, the majority of $E.$ $coli$ proteins found in the refractile bodies are of a much higher molecular mass than the 14.4 kd IL-2 protein and can therefore be removed more easily by alternative methods.

The recovery of IL-2 from cell harvest to the particle paste comprising refractile bodies was about 50% in the example shown in Table I. By washing carefully during the processing, recoveries may reach as high as 70%. These results are compared to the recoveries by the currently used process, which range from 20–25%. Furthermore, a purification of about 7.4-fold was also achieved. Lipopolysaccharide assay results indicate that endotoxin levels in the resuspended particle pellet were about 2–20 $\mu g/ml$ (or about 40–400 ng/mg) protein.

TABLE I

| | | | 10 L SCALE | | | | | |
|---|---|---|---|---|---|---|---|---|
| SAMPLE | VOLUME | TOTAL PROTEIN (MG/ML)[A] | IL-2 (MG/ML)[B] | BIOACTIVITY (UNITS/ML)[C] | SPECIFIC ACTIVITY (UNITS/MG PROTEIN) | TOTAL IL-2(g) | RECOVERY (% BY WEIGHT) | FOLD PURIF |
| HARVEST | 0.5 L | 15.6 | 0.88 | $1.1 \times 10^6$ | $7.2 \times 10^4$ | 9.24 | 100 | 1.0 |
| CONCENTRATE | 2.75 L | 58.8 | | $5.0 \times 10^6$ | $8.5 \times 10^4$ | | | |
| DISRUPTATE 1 | 3.12 L | 40.6 | 2.32 | $2.3 \times 10^6$ | $5.7 \times 10^4$ | 7.24 | 78 | 1.0 |
| DIAFILTRATE | 12.12 L | 3.0 | | $4.1 \times 10^4$ | $1.4 \times 10^4$ | | | |
| DISRUPTATE 2 | 2.75 L | 18.7 | 1.60 | $2.0 \times 10^6$ | $1.1 \times 10^5$ | 4.40 | 48 | 1.5 |
| SUPERNATANT 1 | 3.42 L | 13.7 | | $2.7 \times 10^5$ | $2.0 \times 10^4$ | | | |
| RESUSPENSION 1 | 1.5 L | 7.1 | 2.76 | $2.3 \times 10^6$ | $3.3 \times 10^5$ | 4.14 | 45 | 6.9 |
| SUPERNATANT 2 | 2.2 L | 0.13 | | $1.7 \times 10^3$ | $1.3 \times 10^4$ | | | |
| PARTICLE PELLET | 21.4 g | 525 | 219.2 | $9.0 \times 10^8$ | $1.7 \times 10^6$ | 4.69 | 51 | 7.4 |

[A]Lowry, O. H. et al. (1951) J. Biol. Chem. 193:265–275.
[B]Estimated by densitometry scanning on the basis of IL-2 standards run on SDS-PAGE versus samples.
[C]Samples were assayed for the presence of IL-2 activity by methods described in Gillis, S., et al. (1978) J. Immunol. 120:2027–2032.

density between 1.1 and 1.25 g/ml. A temperature of at least 20° C. was maintained prior to and during centrifugation. The mixture was centrifuged at 10,000–20,000 ×g at 1–2 lpm. The resulting pellet containing purified refractile body particles was stored as a frozen paste at −80° C. The refractile body preparation was subsequently characterized by Lowry assay of total protein, bioactivity, SDS-PAGE, and lipopolysaccharide assay.

EXAMPLE II

Purification of Interleukin-2 (IL-2) Containing Refractile Bodies $E.$ $coli$ K12/MM294-1 cells carrying pLW45 (ATCC No. 39,626) as described in commonly owned copending U.S. Pat. No. 4,530,787, filed Oct. 17, 1984 and issued July 23, 1985 to Z. Shaked et al., were grown as described in Example I(A). Refractile bodies were purified by the method detailed in Example I(B).

A. 10-L Scale

The preparation of refractile bodies is characterized at each step of the purification in Table I. Generally, IL-2 protein represents about 50% of the total protein in the purified particles. The other 50% is presumably contributed by $E.$ $coli$ cellular proteins. The Lowry data shown in Table I were some 20% higher than normal B. Higher Specific Activity IL-2 in the Refractile Body Purification of this Invention Purification of refractile bodies from the same fermentation by the method described herein as well as by the method described by Marston et al. gave the following results:

| | TOTAL PROTEIN (MG/ML) | BIO-ACTIVITY (UNITS/ML) | SPECIFIC ACTIVITY (UNITS/MG) |
|---|---|---|---|
| INVENTION REFRACTILE BODY PELLET | 7.1 | $2.9 \times 10^5$ | $4.1 \times 10^5$ |
| MARSTON REFRACTILE BODY PELLET | 42.5 | $2.1 \times 10^5$ | $5.0 \times 10^4$ |

Thus, it is apparent that (1) the additional diafiltration versus deionized water to remove particle associated contaminants and (2) the increased density due to sucrose addition to keep material less dense than refractile bodies from pelleting result in a specific activity of IL-2 over eight times higher than obtained with the previous method.

C. 1000-L Scale

The preparation of refractile bodies is characterized at several steps of the purification in Table II, which represents a first run. Again as in the case of the 10-L growth, IL-2 represents approximately 50% (53.5%) of the total refractile body protein. The final specific activity is slightly lower than, but within experimental variability of, that obtained in the 10-L preparation. Table III shows the recovery of IL-2 from the harvest to the final refractile body pellet obtained after centrifugation of the sucrose suspension at 10,000–20,000×g. Some 11.3% of the initial IL-2 protein as estimated by densitometry scanning of SDS-PAGE separated proteins was recovered while about 25% of the initial IL-2 bioactivity was recovered. In the second run indicated in Tables IV and V and in FIG. 3, the IL-2 represented approximately 50% (45.7%) of the total refractile body protein, and about 17–23% of the initial IL-2 bioactivity and protein, respectively, was recovered.

Figure 3:
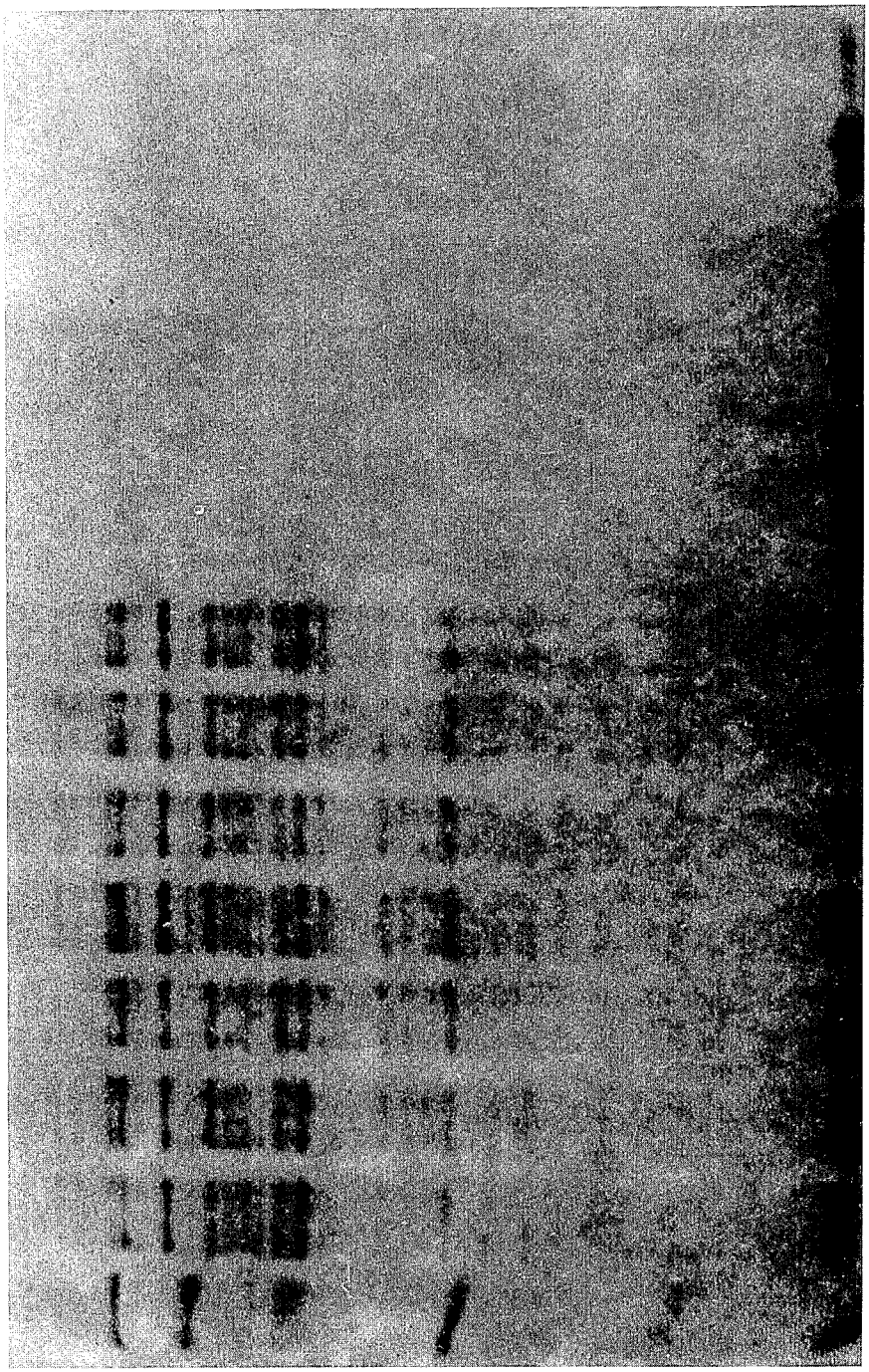
FIG. 3 is an SDS-PAGE reducing gel showing the amount of interleukin-2 obtained at various stages of the process of this invention.

SDS-PAGE (15%, reducing) analysis of the material at each step of refractile body purification is shown in FIG. 3. Lane A of the SDS-PAGE contains molecular mass markers of 94, 67, 43, 30, 20, and 14.4 kilodaltons from top to bottom. Lanes B-E each contain 20 $\mu$g of protein from the cell culture harvest, the concentrated culture, the disruptate, and the diafiltrate, respectively. Lanes F-H each contain 15 $\mu$g of protein showing the two supernatant fractions from the first centrifugation (5 $\mu$g each of the first refractile body pellet are in lanes I and J), and the supernatant from the second centrifugation (5 $\mu$g of the second refractile body pellet are shown in lane K). Lanes L, M, and N contain 3.6, 1.8, and 0.9 $\mu$g, respectively, of purified IL-2 as a standard. The SDS-PAGE indicates that by Lanes I and J representing the first refractile body pellet, the IL-2 is markedly more free of high molecular weight contaminants.

The percentages for recovery indicate a somewhat lower yield of IL-2 in the scaled-up procedure, which is not unexpected due to extensive apparatus involved in processing such large volumes. Recoveries would be expected to improve upon further refinement of the procedure. For example, preliminary results obtained from the fermentation and purification run described in Tables IV and V by the SDS-PAGE suggest that a second centrifugation of the sucrose supernatant yielded pellets with additional refractile bodies. As much as 50–80% of the first pellet mass may be obtained by additional centrifugation. Initial characterizations of this material indicated that it had a purity comparable to that of the first pellet (see FIG. 3, lanes J and K). The figure shows that the IL-2 appears to be quite pure in the disruptate pellet. Estimates of recovery of IL-2 may be as high as about 50%. The majority of the contaminating $E.$ $coli$ proteins are of much higher molecular weight, thereby facilitating further purification of the desired product. The cost reduction and ease in handling realized with the refractile body purification process herein compared with the previously utilized process further enhances its value.

TABLE II

1000 L SCALE (FIRST RUN)

| SAMPLE | TOTAL PROTEIN (MG/ML)[A] | % IL-2 BY DENSITOMETER SCAN | IL-2 (MG/ML)[B] | BIOACTIVITY (UNITS/ML)[C] | SPECIFIC ACTIVITY (U/MG PROTEIN) |
|---|---|---|---|---|---|
| HARVEST | 11.27 | 12.9 | 1.5 | $9.9 \times 10^5$ | $8.8 \times 10^4$ |
| CONCENTRATE | 32.87 | 12.3 | 4.0 | $4.9 \times 10^6$ | $1.5 \times 10^5$ |
| DISRUPTATE | 16.36 | 16.9 | 2.8 | $4.8 \times 10^6$ | $2.9 \times 10^5$ |
| SUCROSE SUPERNATANT | 10.14 | 13.6 | 1.4 | $1.4 \times 10^6$ | $1.4 \times 10^5$ |
| SUCROSE PELLET | 10.27 | 53.5 | 5.5 | $9.4 \times 10^6$ | $9.2 \times 10^5$ |

[A]Lowry, O. H. et al. (1951) J. Biol. Chem. 193:265–275.
[B]Estimated by densitometry scanning on the basis of IL-2 standards run on SDS-PAGE versus samples.
[C]Samples were assayed for the presence of IL-2 activity by methods described in Gillis, S., et al. (1978) J. Immunol. 120:2027–2032.

TABLE III

1000 L SCALE RECOVERY (FIRST RUN)

| SAMPLE | TOTAL PROTEIN (G) | TOTAL IL-2 PROTEIN (G) | TOTAL BIOACTIVITY (UNITS) | RECOVERY (% BY WEIGHT- % BY ACTIVITY) | FOLD PURIFICATION |
|---|---|---|---|---|---|
| HARVEST | 11,300 | 1500 | $9.9 \times 10^{11}$ | 100 | 1 |
| PARTICLE REFRACTILE BODY PELLET | 266 | 169.2 | $2.5 \times 10^{11}$ | 11.3–25 | 4.8 |

TABLE IV

1000 L SCALE (SECOND RUN)

| SAMPLE | TOTAL PROTEIN (MG/ML)[A] | % IL-2 BY DENSITOMETER SCAN | IL-2 (MG/ML)[B] | BIOACTIVITY (UNITS/ML)[C] | SPECIFIC ACTIVITY (UNITS/MG IL-2) |
|---|---|---|---|---|---|
| HARVEST | 9.1 | 12.5 | 1.14 | $1.7 \times 10^6$ | $1.9 \times 10^5$ |
| CONCENTRATE | 29.3 | 15.5 | 4.54 | $4.9 \times 10^6$ | $1.7 \times 10^5$ |
| DISRUPTATE | 26.5 | 15.0 | 3.98 | $5.6 \times 10^6$ | $2.1 \times 10^5$ |
| DIAFILTRATE | 13.8 | 19.2 | 2.65 | $2.6 \times 10^6$ | $1.9 \times 10^5$ |
| SUCROSE SUPERNATANT | 6.0 | 12.8 | 0.77 | $1 \times 10^6$ | $1.7 \times 10^5$ |
| SUCROSE PELLET | 3.0 | 45.7 | 1.38 | $1.5 \times 10^6$ | $5.0 \times 10^5$ |

[A]Lowry, O. H. et al. (1951) J. Biol. Chem. 193:265–275.
[B]Estimated by densitometry scanning on the basis of IL-2 standards run on SDS-PAGE versus samples.
[C]Samples were assayed for the presence of IL-2 activity by methods described in Gillis, S., et al. (1978) J. Immunol. 120:2027–2032.

TABLE V

| | 1000 L SCALE RECOVERY (SECOND RUN) | | | | |
|---|---|---|---|---|---|
| SAMPLE | TOTAL PROTEIN (G) | TOTAL IL-2 PROTEIN (G) | TOTAL BIOACTIVITY (UNITS/ML) | RECOVERY (% BY WEIGHT) | FOLD PURIFICATION |
| HARVEST | 9,090 | 1140 | $1.7 \times 10^{12}$ | 100 | 1 |
| PARTICLE REFRACTILE BODY PELLET | 577 | 264 | $2.9 \times 10^{11}$ | 17-23 | 3.8 |

EXAMPLE III

Formulation of Purified Interleukin-2 (IL-2)

Following the isolation of the particle paste containing refractile bodies described in Example II.C., the paste was further processed to obtain highly purified IL-2 protein. Initially, the paste was solubilized in phosphate buffered saline containing 5% SDS. The solubilized material was centrifuged at 25,000-35,000×g to remove insoluble materials. The supernatant from the centrifugation was reduced by the addition of solid DTT to a final concentration of 50 mM and of EDTA to 2 mM. The pH of the solution was adjusted to 8.5±0.1 with NaOH and then heated to 50±5° C. for 20 minutes under nitrogen. Following the reduction, the reaction was cooled to about 25° C. and the pH was readjusted to 5.5±0.1 using glacial acetic acid.

Chromatographic separation of the higher molecular weight contaminants was achieved next using a Sephacryl®S-200 column. The solubilized and reduced refractile body protein was loaded onto the column and fractions were collected into clean, depyrogenated vessels using an elution buffer containing 50 mM acetate pH 5.5, 1 mM EDTA and 0.1% SDS. Peak fractions (those falling within 70% of the maximum peak height) were pooled and subjected to a controlled oxidation as follows: The S-200 protein pool and iodosobenzoic acid, in a molar ratio of 1:1.6, respectively, were added to a reaction vessel containing 10 mM sodium phosphate, 0.1% SDS and 1 mM EDTA. The pH was controlled at 7.8±0.2 with 0.5N NaOH during oxidation and adjusted to 5.5±0.2 when oxidation was completed. Since oxidized IL-2 is more hydrophilic than reduced IL-2, the progress of the oxidation reaction was monitored by RP-HPLC.

Oxidized IL-2 was concentrated using a hollow fiber ultrafiltration unit with a 10,000 molecular weight cutoff. The protein was then diafiltered against 0.1% SDS, 50 mM acetate pH 5.5 and 1 mM EDTA for three volume exchanges. In preparation for the subsequent HPLC purification, the pH of the diafiltered protein was lowered to 3 or less using glacial acetic acid and filtered through a 0.45 μm filter.

Preparative HPLC using a Vydac C4 bonded phase silica gel column supplied with two solvents was the next step in the IL-2 purification scheme. Solvent 1 was 6% acetic acid and 10% 2-propanol in distilled water, and solvent 2 was 6% acetic acid and 94% 2-propanol in distilled water. After pumping solvent 1 for 30 minutes, the acidified IL-2 protein was loaded. The column was developed with a gradient of solvents 1 and 2 and the protein which eluted at about 40% solvent 2 was pooled into a depyrogenated graduated cylinder. Pooled protein was diluted by slowly adding it to a stirred buffer solution containing 50 mM acetate pH 5.5, 1 mM EDTA and 0.1% SDS that had 14 times the volume of the HPLC pool. Dilution was required due to the sensitivity of the hollow-fiber ultrafiltration unit used for concentration in the next step to organic solvents present in the HPLC pool.

The diluted HPLC pool was concentrated using a hollow-fiber ultrafiltration unit with a 10,000 molecular weight cutoff. The concentrate was diafiltered against 50 mM acetate pH 5.5, 1 mM EDTA and 0.1% SDS with three volume exchanges.

The final chromatographic step in the purification of IL-2 involved a second Sephacryl®S-200 column. The primary objective of this column was to separate the IL-2 monomer fractions from higher molecular weight oligomers of the protein. The column was eluted with buffer containing 50 mM acetate pH 5.5, 1 mM EDTA and 0.1% SDS, and IL-2 monomer fractions were pooled. Immediately preceding formulation, the protein was diafiltered against 10 mM sodium phosphate pH 7.5 until the SDS level was in the range of 100-200 μg/mg protein.

Purified IL-2 was formulated in 10 mM sodium phosphate pH 7.5 with 5% mannitol (w/v). It was prefiltered through a 0.45 μm filter and sterile filtered through a 0.22 μm filter. Finally, the product was lyophilized to dryness in the container vial for storage at 4° C. The purified and formulated IL-2 protein produced in this manner was found to be 97% pure by HPLC and 99% pure IL-2 monomer by either reduced or non-reduced SDS-PAGE. The specific activity was $2.3 \times 10^6$ units/mg protein and the level of residual SDS was 181 μg SDS/mg IL-2, 100-200 μg SDS/mg IL-2 being required to maintain the desired IL-2 solubility. The amino-terminal amino acid sequence and the amino acid composition of the final product agreed with theoretical predictions.

EXAMPLE IV

Purification of Human Fibroblast Interferon (IFN-β) Containing Refractile Bodies E. coli K12/MM294-1 cells carrying pSY2501 (ATTC No. 39,517) as described in U.S. Pat. No. 4,518,584, assigned to Cetus Corporation, were grown as described in Example 1(A).

A. Purification of Refractile Bodies

Refractile bodies were purified by the method detailed in Example I(B)(1) with some modifications. Cells were disrupted in the homogenizer by three passes at 7500 psi. The system was rinsed with deionized water and the lysate was brought to a final volume of 5 L with deionized water (Disruptate 1). Diafiltration versus five volumes of deionized water (diafiltered disruptate) was followed by concentration of the cell particle material and a rinse of the system with 0.75 L 10 mM EDTA. The final volume of this diafiltered cellular concentrate was 2.1 L. The concentrate was redisrupted by three passes at 7500 psi in the homogenizer, and an equal volume of 63% sucrose and 2 mM EDTA was added to give a volume of 5.0 L (Disruptate 2). The mixture was centrifuged at 40,000 rpm in a Sharples centrifuge at about 100 ml/min. The system was rinsed with 1.0 L 10 mM EDTA. The final pellet containing purified refractile body particles (Final Pellet) was stored as a frozen paste at −80° C.

B. Characterization of Refractile Body Preparation

The preparation of refractile bodies is characterized at each step of the purification in Table VI. It appears that IFN-β

(iv) $(NH_4)_2SO_4$;

2. the fermenter feed and addition vessels were then sterilized according to standard operating procedures;
3. the fermenter was cooled and inoculated with frozen or seed *E. coli* culture;
4. no tetracycline was added to the fermentation

TABLE VI

10 L SCALE

| SAMPLE | VOLUME | TOTAL PROTEIN (MG/ML)[A] | IFN-β (MG/ML)[B] | BIOACTIVITY (UNITS/ML)[C] | SPECIFIC ACTIVITY (UNITS/MG IFN-β) | TOTAL IFNβ (g) | RECOVERY (% BY WEIGHT) | FOLD PURIF |
|---|---|---|---|---|---|---|---|---|
| HARVEST | 10.64 L | 5.4 | 0.19 | — | — | 2.02 | — | — |
| CONCENTRATE | 3.15 L | 19.5 | 0.68 | $2.4 \times 10^8$ | $1.2 \times 10^7$ | 2.14 | 100 | 1.0 |
| DISRUPTATE 1 | 3.78 L | 13.8 | 0.62 | $1.8 \times 10^8$ | $1.3 \times 10^7$ | 2.34 | 109 | 1.28 |
| DIAFILTRATE | 28.0 L | 0.5 | N.D. | $1.2 \times 10^7$ | $2.4 \times 10^7$ | N.D. | 0 | N.A. |
| DIAFILTERED CELLULAR CONCENTRATE | 2.1 L | 16.4 | 1.02 | $3.2 \times 10^8$ | $2.0 \times 10^7$ | 2.14 | 100 | 1.8 |
| DISRUPTATE 2 | 5.0 L | 6.7 | 0.44 | $1.3 \times 10^8$ | $1.9 \times 10^7$ | 2.20 | 102 | 1.9 |
| SUPERNATANT | 5.8 L | 4.2 | 0.08 | $4.2 \times 10^7$ | $1.0 \times 10^7$ | 0.46 | 22 | |
| PARTICLE PELLET | 55.3 g | 8.97 g | 1.54 | $7.3 \times 10^{11}$ | $8.1 \times 10^7$ | 1.71 | 85 | 4.9 |

[A]Lowry, O. H. et al. (1951) J. Biol. Chem. 193:265-275.
[B]Estimated by densitometry scanning of IFNβ standards run on SDS-PAGE versus samples.
[C]Samples were assayed for the presence of IFN-β antiviral activity by methods described in W. E. Stewart, "The Interferon System", Springer-Verlag, p17-18 (1979).
N.D. = not detectable
N.A. = not applicable represented about 17% of the total protein in the purified particles. The other 83% was presumably contributed by *E. coli* cellular proteins. The recovery of IFN-β from cell harvest to the particle paste comprising refractile bodies was 85%, indicating that almost all of the IFN-β produced by *E. coli* carrying pSY2501 was contained in refractile bodies. The additional contents of these refractile bodies limited the degree of purification of IFN-β which could be achieved by simple isolation of refractile bodies. However, most contaminants are of a much higher molecular mass and can therefore be removed more easily by alternative methods. Furthermore, this simple, high-recovery "front end" process for recovering recombinant IFN-β does not require the use of an aliphatic alcohol to extract this lipophilic protein from the aqueous medium in which it is produced. The next example illustrates the further developed high-recovery "front end" process wherein an organic extraction is employed.

EXAMPLE V

Purification of Human Fibroblast Interferon (IFN-β) Containing Refractile Bodies This example delineates the alternative expanded front-end process for recovery of the final pellet containing refractile bodies having approximately 80% (81.4%) IFN-β. *E. coli* K12/MM294-1 cells carrying pSY2501 (ATCC No. 39,517) as described in U.S. Pat. No. 4,518,584, assigned to Cetus Corporation, were grown essentially as described in Example 1(A) for a 1000-liter fermentation run. The differences between Example 1(A) and that for cell growth in this example were the following:

1. Once the fermenter was filled with water to the operating volume, the following trace elements were added:
(i) $ZnSO_4.7H_2O$
$MnSO_4.H_2O$
$CuSO_4.5H_2O$
(ii) $Na_3$ Citrate.$2H_2O$
(iii) $KH_2PO_4$ broth;
5. 100 μM, rather than, 72 μM $FeSO_4.7H_2O$ was used;
6. 20 mM, rather than 3 mM $MgSO_4.7H_2O$ was used;
7. at approximately 15 hours after fermentation was begun, the pH was adjusted to 6.8;
8. optical density measurements and residual glucose measurements on samples were taken at 14-16 hours and approximately 1 hour intervals thereafter; and
9. the cultures were harvested when glucose consumption reached 40±6 g/l.

EXPANDED FRONT-END PROCESS

The general purification scheme for a heterologous protein utilizing the expanded front-end process for the isolation of refractile bodies is diagrammed in FIG. 2. As indicated in Example I(B), supra, the selection of the denaturing agent for solubilizing the desired protein form the inclusion body preparation as well as the additional steps required in the purification process will be dependent upon the nature of the protein and have been described to some extent by Marston et al., supra, and Kleid et al., supra.

At various steps of the expanded front-end process used in this example, the refractile body preparations were characterized by Lowry assay of total protein bioactivity, SDS-PAGE and lipopolysaccharide assay. Table VII characterizes preparation of refractile bodies at various steps of the purification up to the final pellet. From the densitometer scan of SDS-PAGE results, it appears that IFN-β represented about 81.4% of the total protein in the final pellet.

Cultures were concentrated approximately 5-10 fold by circulating the harvest material (Harvest) under pressure through UF cross-flow filtration cartridges with a 100K molecular weight cutoff (Concentrate). Cells were disrupted by 3 passes through a Manton-Gaulin high-pressure homogenizer at 6,000 to 8,000 psi (Disruptate I).

EDTA was added to the disruptate to a final concentration of 5 mM. The suspension was then diafiltered against 5 volumes of deionized water (diafiltered disruptate).

EDTA was then added to a final concentration of 2 mM. Octanol was added to 1% (v/v) to kill any residual live bacteria in the diafiltered product. The suspension was redisrupted by passing it twice through the Manton-Gaulin high-pressure homogenizer at 6,000–8,000 psi (Disruptate II).

Sucrose was added to the redisruptate to a final concentration of 23% (wt/wt), creating a final density gradient between 1.1 and 1.25 g/ml (Sucrose Suspension). The mixture was centrifuged at 10,000 to 15,000 xg, and the particle pellet or paste was collected (Particle Pellet). As indicated by densitometer scan the particle pellet contained approximately 20.4% IFN-$\beta$.

The particle pellet was then solubilized in phosphate buffered saline with 2% SDS. Solid DTT and EDTA were added to a final concentration of 10 mM and 2 mM, respectively. The suspension was heated to 50°±5° C. for 10 minutes under nitrogen. The reaction mixture was then cooled to approximately 25° C., and then the pH of the mixture was adjusted to 7.4.

A volume of 2-butanol equal to the total volume of the suspension was measured. The suspension and organic solution were pumped separately but simultaneously at flow rates of 1.1 to 1.3 liters per minute through a static mixer and then into a continuous centifuge (Westfalia at approximately 11,770 xg) for phase separation. The 2-butanol-rich phase containing the IFN-$\beta$ was collected (Organic Extract).

The 2-butanol extract was mixed with 2.5 volumes of 0.1% SDS in phosphate-buffered saline. Solid DTT was added to a final concentration of 2 mM. The pH of the organic extract/buffer solutions was adjusted to 6.2±0.1 with glacial acetic acid (Acid Precipitate).

The mixture was then centrifuged (Sharples centrifuge at 13,200 xg) for approximately 2–6 hours. The final pellet was then collected (Final Pellet) containing approximately 81% IFN-$\beta$.

DOWNSTREAM PROCESSING

The final pellet was then re-suspended with 5% SDS in 50 mM phosphate buffer and 5 mM EDTA. Solid DTT was added to a final concentration of 20 mM, and the pH was adjusted to 8.5 with NaOH. The suspension was heated to 50°±5° C. for 10 minutes under nitrogen, and then cooled to approximately 25° C. The pH was then adjusted to a pH of 5.5 with glacial acetic acid, and the solution was filtered through a 0.65 $\mu$m filter.

The filtrate was then processed by pre-column chromatography by loading a Sephacryl® S200 column and collecting fractions into clean, depyrogenated vessels using an elution buffer that is composed of 50 mM acetate, pH 5.5, 1 mM EDTA and 1% SDS. The fractions containing the IFN-$\beta$ monomer were pooled.

The pre-column pool was then concentrated by using a hollow-fiber ultrafiltration unit with a 10K molecular weight cut-off.

The concentrated pre-column pool was then oxidized using iodosobenzoic acid (IBA). The oxidation was effected by adding equimolar amounts of protein and IBA into a reaction vessel containing 2 mM sodium pyrophosphate, 0.1% SDS and 1 mM EDTA. A 20 $\mu$M excess of IBA was present at the end of the oxidation. The pH was controlled at 9.0±0.1 with NaOH during oxidation, and adjusted to 5.5±0.2 with glacial acetic acid when the oxidation was completed.

The protein was then concentrated using a hollow-fiber ultrafiltration unit with a 10K molecular weight cut-off.

The protein was then loaded onto the main column (Sephacryl® S200-A), and fractions were collected into clean, depyrogenated vessels using an elution buffer that is composed of 50 mM acetate, pH 5.5, 1 mM EDTA and 0.1% SDS.

A SDS-PAGE was performed on samples from each fraction tube starting from the beginning of the peak to be pooled to the end of the peak. Using the SDS-PAGE results, the fractions containing no high molecular weight contaminants were determined. Those fractions were then pooled.

The main column pool was then concentrated by using a hollow-fiber ultrafiltration unit with a 10K molecular weight cut-off.

The above procedure performed with the main column was repeated on a Sephadex® G-75 column. Using the SDS-PAGE results, the fractions containing neither low nor high molecular weight contaminants were pooled.

A Sephadex® G-25 column was then equilibrated with 1 mM NaOH and loaded with the Sephadex® G-75 pool. Using the process chromatogram, the IFN-$\beta$ peak was collected. The product was formulated within 15 minutes from this desalting process.

The purified IFN-$\beta$ was formulated with Normal Serum Albumin (Human) USP (NSA) and 50% Dextose Monohydrate. Normal Serum Albumin was diluted with water for injection to give a final concentration of 1.25% for 0.05 and 0.25 mg/ml IFN-$\beta$ formulations or of 5.0% for a 1.00 mg/ml IFN-$\beta$ formulation. The pH of the diluted NSA solution was adjusted to 12.0±0.5 with 10% NaOH.

The IFN-$\beta$ was immediately added to the NSA solution, and the pH of the mixture was adjusted to 7.5±0.3 with 3–6N HCl. The calculated amount of dextrose was then added.

The formulated product was pre-filtered through a 0.45 $\mu$m filter and then filtered through a sterile 0.22 $\mu$m filter within 4 hours.

Then sterilized vials with sterilized stoppers and components were aseptically filled with the IFN-$\beta$ formulations under sanitary and sterile conditions that were environmentally monitored.

The vials were placed in a lyophilizer where appropriate thermocouples were attached. The vials were frozen to between −35° and −45° C. The lyophilization cycle was completed and the vials were mechanically sealed under a vacuum.

TABLE VII

| | 1000 L SCALE | | | | |
|---|---|---|---|---|---|
| SAMPLE | TOTAL PROTEIN (MG/ML)$^{(A)}$ | IFN-$\beta$ (MG/ML)$^{(B)}$ | BIOACTIVITY (UNITS/ML)$^{(C)}$ | SPECIFIC ACTIVITY (UNITS/MG IFN-$\beta$) | % IFN-$\beta$ BY DENSITOMETER SCAN |
| HARVEST | 7.31 | 0.32 | $3.3 \times 10^6$ | $1.0 \times 10^7$ | 6.6 |
| CONCENTRATE | 24.56 | 1.24 | $1.8 \times 10^7$ | $1.4 \times 10^7$ | 6.4 |

TABLE VII-continued

1000 L SCALE

| SAMPLE | TOTAL PROTEIN (MG/ML)[A] | IFN-$\beta$ (MG/ML)[B] | BIOACTIVITY (UNITS/ML)[C] | SPECIFIC ACTIVITY (UNITS/MG IFN-$\beta$) | % IFN-$\beta$ BY DENSITOMETER SCAN |
|---|---|---|---|---|---|
| DISRUPTATE I | 15.65 | 1.10 | $5.6 \times 10^6$ | $5.1 \times 10^6$ | 6.3 |
| DIAFILTRATE | 11.53 | 0.81 | $8.9 \times 10^6$ | $1.1 \times 10^7$ | 6.6 |
| DISRUPTATE II | 11.09 | 0.66 | $5.0 \times 10^6$ | $7.6 \times 10^6$ | 6.4 |
| SUCROSE SUSPENSION | 11.42 | 0.76 | $8.9 \times 10^6$ | $1.2 \times 10^7$ | 6.8 |
| PARTICLE PELLET | 4.07 | 0.64 | $1.5 \times 10^7$ | $2.3 \times 10^7$ | 20.4 |
| ORGANIC EXTRACT | 0.57 | 0.21 | $6.3 \times 10^6$ | $3.0 \times 10^7$ | 88.3 |
| ACID PRECIPITATE | 0.18 | 0.05 | $1.8 \times 10^6$ | $3.6 \times 10^7$ | 80.8 |
| FINAL PELLET | 2.68 | 2.12 | $5.6 \times 10^7$ | $2.7 \times 10^7$ | 81.4 |

[A]Lowry, O. H. et al. (1951) J. Biol. Chem. 193:265-275.
[B]Estimated by densitometry scanning on the basis of IFN-$\beta$ standards run on SDS-PAGE versus samples.
[C]Samples were assayed for the presence of IFN-$\beta$ antiviral activity by methods described in W. E. Stewart, "The Interferon System," Springer-Verlag, pp. 17 & 18 (1979).

In summary, it can be seen that the present invention provides an efficient process for isolating refractile bodies containing heterologous proteins from the host disruptate in which the refractile bodies are contained. In the process herein, cost reduction and ease in handling are realized.

Modifications of the above-described modes for carrying out the invention which are obvious to those skilled in the field of pharmaceutical formulation or related fields are intended to be within the scope of the following claims.

What is claimed is:

1. A process for recovering a refractile material containing a heterologous protein from a host microorganism cell culture transformed to produce said protein, said process comprising:
    (a) disrupting the cell wall and cell membrane of the microorganism;
    (b) removing greater than 99% by weight of the salts from said disruptate;
    (c) redisrupting the desalted disruptate;
    (d) adding a material to the disruptate to increase the density or viscosity of, or to create a density or viscosity gradient in, the liquid within the disruptate; and
    (e) separating the refractile material from the cellular debris by high-speed centrifugation.

2. The process of claim 1 wherein step (a) is accomplished in the presence of 1-octanol.

3. The process of claim 2 further comprising the step of adding distilled water to the disruptate after step (a) and during step (b).

4. The process of claim 3 wherein step (b) is accomplished by diafiltration.

5. The process of claim 1 wherein step (b) is accomplished by centrifuging the cell membrane and resuspending in deionized water.

6. The process of claim 1 wherein step (d) is accomplished by adding a material to increase the density of the liquid to a $\rho$ of from about 1.1 to 1.3 g/cm$^3$.

7. The process of claim 6 wherein the density of the liquid is increased to a $\rho$ of from 1.13 to 1.17 g/cm$^3$.

8. The process of claim 7 wherein the material is one or more sugars.

9. The process of claim 8 wherein the sugar is sucrose.

10. The process of claim 9 wherein a mixture of sucrose and glycerol is added to form a two-phase system.

11. The process of claim 1 wherein step (d) is accomplished by adding a material to increase the viscosity of the liquid to between 5 and 10 cps.

12. The process of claim 1 wherein the protein is interferon-$\beta$ or interleukin-2.

13. The process of claim 1 wherein the protein is interleukin-2.

14. The process of claim 13 wherein the interleukin-2 is des-ala-ser$_{125}$ IL-2.

15. The process according to claim 1 further comprising the following steps:
    (f) solubilizing the refractile material under reducing conditions;
    (g) organically extracting the solubilized refractile material; and
    (h) isolating said refractile material from the extractant.

16. The process according to claim 15 wherein step (f) is accomplished with a solubilizing agent in an aqueous buffer in the presence of a reducing agent.

17. The process of claim 16 wherein the solubilizing agent is SDS and the aqueous buffer is phosphate buffered saline.

18. The process according to claim 16 wherein the percentage range of the solubilizing agent is 1 to 5%.

19. The process according to claim 17 wherein SDS is at a concentration of approximately 2%.

20. The process according to claim 15 wherein step (f) is carried out with DTT as the reducing agent in a concentration of from 5 to 20 mM.

21. The process according to claim 20 wherein DTT is at a concentration of 10 mM.

22. The process according to claim 15 wherein step (f) is carried out in the presence of a chelating agent in a concentration range of between 1 and 5 mM.

23. The process according to claim 22 wherein the chelating agent is EDTA in a concentration of approximately 2 mM.

24. The process according to claim 15 wherein step (f) is carried out at an alkaline pH ranging from about 8.5 to about 9.5.

25. The process according to claim 24 wherein the pH is approximately 9.

26. The process according to claim 15 wherein the reducing conditions of step (f) include an elevated temperature of between 45°–55° C.

27. The process according to claim 15 comprising the additional step of adjusting the pH to between 7 and 7.8 before beginning the organic extraction of step (g).

28. The process of claim 15 wherein step (g) is accomplished by using 2-butanol as the organic extractant.

29. The process of claim 28 wherein the volume ratios of the extractant to the suspension are in a range of about 0.8:1 to about 3:1.

30. The process of claim 28 wherein said volume ratios are equimolar.

31. The process of claim 15 wherein step (g) is accomplished by employing an acid precipitation step followed by centrifugation.

32. The process of claim 31 wherein the acid precipitation step is accomplished by adjusting the pH to the range of from 5 to 6.5.

33. The process of claim 32 wherein the pH is adjusted to $6.2 \pm 0.1$ with glacial acetic acid.

34. The process of claim 31 wherein the centrifugation is carried out at between 10,000 and 15,000 xg.

35. The process of claim 34 wherein the centrifugation is carried out for from 2 to 6 hours.

36. The process of claim 31 wherein the acid precipitation is accomplished in the presence of a solubilizing agent in an aqueous buffer and in the presence of a reducing agent.

37. The process of claim 36 wherein the solubilizing agent is SDS, the aqueous buffer is phosphate buffered saline and the reducing agent is DTT.

38. The process according to claim 15 wherein the protein is interferon-$\beta$ or interleukin-2.

39. A process for recovering a refractile material containing recombinant IL-2 or recombinant IFN-$\beta$ from *E. coli* transformed to produce it, said process comprising:
(a) concentrating the host *E. coli* cells by cross-flow filtration;
(b) disrupting the cell wall and cell membrane of the *E. coli* by a disrupting means in the presence of 1% 1-octanol;
(c) adding distilled water to the disruptate;
(d) diafiltering the disruptate until greater than 99% of the salts are removed using continuous addition of distilled water such that the rate of addition of water equals the diafiltration rate;
(e) redisrupting the desalted disruptate;
(f) adding sucrose to increase the density of the liquid to a $\rho$ of between 1.13 and 1.17 g/cm$^3$; and
(g) separating the refractile material from the cellular debris by high speed centrifugation.

40. The process of claim 39 further comprising the steps of (h) solubilizing the IL-2 or IFN-$\beta$ in the refractile material with an aqueous solution of a solubilizing agent which forms a water-soluble complex with the IL-2 or IFN-$\beta$, said solution containing a reducing agent; (i) separating the IL-2 or IFN-$\beta$ from the resulting solution in the presence of the reducing agent; (j) oxidizing the product of step (i); and (k) purifying the oxidized product by reverse-phase high performance liquid chromatography.

41. The process of claim 40 wherein said solubilizing agent is sodium dodecyl sulfate or sodium laurate sarcosine, the reducing agent is dithiothreitol, step (i) is carried out by gel filtration or reverse-phase high performance liquid chromatography, and step (j) is carried out using iodosobenzoic acid.

42. The process of claim 41 wherein step (i) is carried out by isolating an IL-2 or IFN-$\beta$ containing fraction from the solution by gel filtration and purifying the resulting IL-2 or IFN-$\beta$ from the fraction by reverse-phase high performance liquid chromatography, and after step (k) the purified product is formulated and lyophilized.

43. The process of claim 39 further comprising the following steps:
(h) solubilizing the refractile material from step (g) under reducing conditions;
(i) extracting the solubilized refractile material with 2-butanol; and
(j) isolating the extracted refractile material by acid precipitation followed by centrifugation.

44. The process of claim 43 further comprising the steps of (k) solubilizing the extracted refractile material from step (j) under reducing conditions and at an alkaline pH; (l) adjusting the pH to approximately 5.5; (m) separating the IL-2 or IFN-$\beta$ from the solution in the presence of a reducing agent; (n) oxidizing the product of step (m); (o) purifying the oxidized product by protein purification procedures.

45. A process according to claim 44 wherein step (n) is carried out using iodosobenzoic acid and step (o) is carried out by gel filtration, reverse-phase high performance liquid chromatography (RP-HPLC) or by a combination of gel filtration and RP-HPLC.

46. The process of claim 45 wherein the purified product from step (o) is formulated and lyophilized.

* * * * *